(12) United States Patent
Shortt et al.

(10) Patent No.: US 7,554,656 B2
(45) Date of Patent: Jun. 30, 2009

(54) METHODS AND SYSTEMS FOR INSPECTION OF A WAFER

(75) Inventors: David Shortt, Milpitas, CA (US); Stephen Biellak, Sunnyvale, CA (US); Alexander Belyaev, Mountain View, CA (US)

(73) Assignee: KLA-Tencor Technologies Corp., Milpitas, CA (US)

(*) Notice: Subject to any disclaimer, the term of this patent is extended or adjusted under 35 U.S.C. 154(b) by 267 days.

(21) Appl. No.: 11/244,451

(22) Filed: Oct. 6, 2005

(65) Prior Publication Data

US 2007/0081151 A1    Apr. 12, 2007

(51) Int. Cl.
*G01N 21/00* (2006.01)

(52) U.S. Cl. .............. 356/237.5; 356/237.2

(58) Field of Classification Search .......... None
See application file for complete search history.

(56) References Cited

U.S. PATENT DOCUMENTS

| | | | |
|---|---|---|---|
| 4,449,818 A | 5/1984 | Yamaguchi | |
| 4,740,079 A | 4/1988 | Koizumi et al. | |
| 4,794,265 A | 12/1988 | Quackenbos et al. | |
| 4,893,932 A | 1/1990 | Knollenberg | |
| 4,898,471 A | 2/1990 | Vaught et al. | |
| 4,929,845 A | 5/1990 | Amir et al. | |
| 4,966,457 A | 10/1990 | Hayano et al. | |
| 5,058,982 A | 10/1991 | Katzir | |
| 5,389,794 A | 2/1995 | Allen et al. | |
| 5,416,594 A | 5/1995 | Gross et al. | |
| 5,424,838 A | 6/1995 | Siu | |
| 5,530,550 A | 6/1996 | Nikoonahad et al. | |
| 5,623,341 A | 4/1997 | Hunt | |
| 5,650,614 A | 7/1997 | Yasutake et al. | |
| 5,798,829 A | 8/1998 | Vaez-Iravani | |
| 5,936,726 A * | 8/1999 | Takeda et al. | 356/237.2 |
| 6,104,481 A | 8/2000 | Sekine et al. | |
| 6,201,601 B1 * | 3/2001 | Vaez-Iravani et al. | 356/237.4 |
| 6,266,137 B1 * | 7/2001 | Morinaga | 356/237.1 |
| 6,271,916 B1 | 8/2001 | Marxer et al. | |
| 6,292,259 B1 | 9/2001 | Fossey et al. | |
| 6,292,260 B1 | 9/2001 | Lin et al. | |

(Continued)

FOREIGN PATENT DOCUMENTS

DE    4123916    1/1992

(Continued)

OTHER PUBLICATIONS

Dialog Search conducted Jul. 15, 2002.

(Continued)

*Primary Examiner*—Michael P Stafira
(74) *Attorney, Agent, or Firm*—Ann Marie Mewherter (57) ABSTRACT

Methods and systems for inspection of a wafer are provided. One method includes illuminating the wafer with light at a first wavelength that penetrates into the wafer and light at a second wavelength that does not substantially penetrate into the wafer. The method also includes generating output signals responsive to light from the wafer resulting from the illuminating step. In addition, the method includes detecting defects on the wafer using the output signals. The method further includes determining if the defects are subsurface defects or surface defects using the output signals.

21 Claims, 4 Drawing Sheets

U.S. PATENT DOCUMENTS

| | | | |
|---|---|---|---|
| 6,486,946 | B1 | 11/2002 | Stover et al. |
| 6,509,964 | B2 | 1/2003 | Wiles et al. |
| 6,509,965 | B2 | 1/2003 | Fossey et al. |
| 6,538,730 | B2 | 3/2003 | Vaez-Iravani et al. |
| 6,587,192 | B2 | 7/2003 | Isozaki et al. |
| 6,611,328 | B2 | 8/2003 | Isozaki et al. |
| 6,639,662 | B2 | 10/2003 | Vaez-Iravani et al. |
| 6,654,111 | B2 | 11/2003 | Isozaki et al. |
| 6,956,644 | B2 * | 10/2005 | Biellak et al. ............ 356/237.4 |
| 2001/0052975 | A1 * | 12/2001 | Biellak et al. ............ 356/237.3 |
| 2005/0018183 | A1 * | 1/2005 | Shortt ..................... 356/239.1 |
| 2006/0066843 | A1 * | 3/2006 | Guetta et al. ............ 356/237.2 |

FOREIGN PATENT DOCUMENTS

| | | |
|---|---|---|
| EP | 0624787 | 3/1994 |
| EP | 1318392 | 6/2003 |
| JP | 07-128244 | 5/1995 |
| JP | 07-270328 | 10/1995 |
| JP | 11-237225 | 8/1999 |
| JP | 11/237344 | 8/1999 |
| JP | 2000-216208 | 8/2000 |
| JP | 2000-352507 | 12/2000 |
| WO | 97/12226 | 4/1997 |
| WO | 97/33158 | 9/1997 |
| WO | 00/02037 | 1/2000 |

OTHER PUBLICATIONS

Dialog Search conducted Jul. 16, 2002.

International Search Report, PCT/US02/20881, mailed Sep. 23, 2002.

Yatsugake et al., "Surface Inspection System for Estimation of Wafer," Hitachi Electronics Engineering Technical Report, vol. 11, Jan. 1996, pp. 21-26.

Figure by Hitachi Electronics Co., Ltd., included in presentation by Etsuro Morita entitled "Exploration of COP and COP Defect Crystal Originated Particles," 6th Int'l Workshop on 300 Millimeter Wafers, Dec. 1996.

Partial European Search Report, EP 98947155.2, mailed Oct. 18, 2000.

Richmond, "Silicon-On-Insulator Technology," SysOpt.com, Nov. 2000, 11 pages.

International Search Report for Appln. No. PCT/US06/38568 dated Oct. 10, 2007.

\* cited by examiner

METHODS AND SYSTEMS FOR INSPECTION OF A WAFER

BACKGROUND OF THE INVENTION

1. Field of the Invention

This invention generally relates to methods and systems for inspection of a wafer. Certain embodiments relate to a method for inspection of a wafer that includes illuminating the wafer with different wavelengths at least one of which penetrates into the wafer and at least one of which does not substantially penetrate into the wafer.

2. Description of the Related Art

The following description and examples are not admitted to be prior art by virtue of their inclusion in this section.

Fabricating semiconductor devices such as logic and memory devices typically includes processing a specimen such as a semiconductor wafer using a number of semiconductor fabrication processes to form various features and multiple levels of the semiconductor devices. For example, lithography is a semiconductor fabrication process that typically involves transferring a pattern to a resist arranged on a semiconductor wafer. Additional examples of semiconductor fabrication processes include, but are not limited to, chemical-mechanical polishing, etch, deposition, and ion implantation. Multiple semiconductor devices may be fabricated in an arrangement on a semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits. However, as the dimensions of semiconductor devices decrease, inspection becomes even more important to the successful manufacture of acceptable semiconductor devices because smaller defects can cause the device to fail. For instance, as the dimensions of semiconductor devices decrease, detection of defects of decreasing size has become necessary since even relatively small defects may cause unwanted aberrations in the semiconductor devices.

In the past, it has been extremely difficult to discriminate between surface and subsurface defects on a wafer in a non-destructive manner (e.g., using an optical inspection system). Some approaches that have been used to determine if defects are surface or subsurface defects involve discriminating between crystal originated particles (COPs) and particle surface defects by comparing light scattered through different sets of solid angles and/or incidence angles.

One example of such a wafer inspection system for distinguishing between pits and particles is illustrated in U.S. Pat. No. 6,509,965 to Fossey et al., which is incorporated by reference as if fully set forth herein. The surface inspection system described by Fossey et al. includes a scanner configured to scan a P-polarized light beam across a surface of a workpiece. The system is configured to detect differences in the angular distribution of light scattered from the workpiece and to distinguish particle defects from pit defects based upon these differences. For example, if the defect is a pit, the amount of light scattered and detected by a center channel collector of the system is typically greater than that detected by a back channel collector of the system. Alternatively, if the defect is a particle, the amount of light detected by the center channel collector is typically less than that detected by the back channel collector and/or a forward channel collector of the system.

Another example of a system for discriminating between holes in and particles on a film covering a substrate is illustrated in U.S. Pat. No. 6,486,946 to Stover et al., which is incorporated by reference as if fully set forth herein. This system is configured to direct P-polarized light or light having a strong P-polarized component onto a filmed substrate at two (or more) different incidence angles, one of which is relatively large and the other of which is relatively small as measured from a surface normal. Light that is scattered into a back region of the hemispherical space above the substrate surface is collected and the intensity of the collected light is measured for each of the two incident angles. A defect can then be classified as either a hole in the film or a particle on the film based on the relatively intensities of the collected light. For instance, for holes formed in the film, the back-scattered light intensity at relatively large incidence (i.e., highly oblique incidence) is substantially smaller than the back-scattered light intensity at relatively small incidence (i.e., normal or near normal incidence). For particles, however, there is no such substantial decrease in intensity, and in many cases, the intensity actually increases slightly from small to large incidence. Accordingly, a defect can be classified as either a hole or a particle by measuring backscattered light intensity for both incidence angles and looking for a substantial decrease in intensity. If there is no such decrease, the defect is a particle. On the other hand, if there is a substantial decrease, the defect is a hole.

There are, however, a number of disadvantages to the currently available methods and systems for distinguishing between particle and pit defects. For example, two different types of COPs, one breaking the surface of the wafer and one totally submerged below the surface of the wafer, will both be classified as COPs by the systems and methods that are currently available. Of course, defect review tools and methods can be used to definitively determine if defects are surface or subsurface defects. For example, substantially slow methods such as focused ion beam (FIB) tools can be used to reveal the structure below the surface of the wafer. In addition, scanning electron microscopy (SEM) or atomic force microscopy (AFM) tools can be used to determine if a defect breaks the surface of the wafer, but these tools are also substantially slow. However, a definite need has been expressed for systems that are capable of discriminating between surface and subsurface defects as part of a standard wafer inspection with high accuracy and without using additional and/or substantially slow defect review tools.

Accordingly, it would be advantageous to develop methods and systems for inspection of a wafer that can be used to distinguish between surface and subsurface defects with relatively high accuracy and relatively high throughput.

SUMMARY OF THE INVENTION

The following description of various embodiments of methods, systems, and carrier media is not to be construed in any way as limiting the subject matter of the appended claims.

One embodiment relates to a method for inspection of a wafer. The method includes illuminating the wafer with light at a first wavelength that penetrates into the wafer and light at a second wavelength that does not substantially penetrate into the wafer. The method also includes generating output signals responsive to light from the wafer resulting from the illuminating step. In addition, the method includes detecting defects on the wafer using the output signals. The method further includes determining if the defects are subsurface defects or surface defects using the output signals.

In one embodiment, the first wavelength is a visible wavelength, and the second wavelength is an ultraviolet wavelength. In another embodiment, illuminating the wafer with the light at the first and second wavelengths is performed sequentially. In a different embodiment, illuminating the wafer with the light at the first and second wavelengths is performed simultaneously. In some embodiments, illuminating the wafer includes directing the light at the first and second wavelengths to the wafer at substantially the same angle of incidence. In other embodiments, illuminating the wafer includes directing the light at the first and second wavelengths to the wafer at different angles of incidence.

In one embodiment, the light from the wafer includes scattered light. In another embodiment, generating the output signals includes collecting the light from the wafer at multiple sets of solid angles.

In an additional embodiment, the method includes determining a lateral dimension of the defects using the output signals. In a further embodiment, the method includes determining a depth of the subsurface defects within the wafer using the output signals. In another embodiment, determining if the defects are subsurface defects or surface defects includes comparing the output signals responsive to the light returned from the wafer resulting from illuminating the wafer with the light at the first wavelength and the output signals responsive to the light returned from the wafer resulting from illuminating the wafer with the light at the second wavelength as a function of location on the wafer. Each of the embodiments of the method described above may include any additional step(s) described herein.

Another embodiment relates to a system configured to inspect a wafer. The system includes an illumination subsystem configured to illuminate the wafer with light at a first wavelength that penetrates into the wafer and light at a second wavelength that does not substantially penetrate into the wafer. The system also includes a detection subsystem configured to generate output signals responsive to light from the wafer resulting from illumination of the wafer. In addition, the system includes a processing subsystem configured to detect defects on the wafer using the output signals and to determine if the defects are subsurface defects or surface defects using the output signals.

In one embodiment, the illumination subsystem includes a single light source. In a different embodiment, the illumination subsystem includes more than one light source. One of the more than one light source is configured to generate the light at the first wavelength. Another of the more than one light source is configured to generate the light at the second wavelength. In another embodiment, the first wavelength is a visible wavelength, and the second wavelength is an ultraviolet wavelength.

In some embodiments, the illumination subsystem is configured to illuminate the wafer with the light at the first and second wavelengths sequentially. In other embodiments, the illumination subsystem is configured to illuminate the wafer with the light at the first and second wavelengths simultaneously. In a further embodiment, the illumination subsystem is configured to illuminate the wafer by directing the light at the first and second wavelengths to the wafer at substantially the same angle of incidence. In a different embodiment, the illumination subsystem is configured to illuminate the wafer by directing the light at the first and second wavelengths to the wafer at different angles of incidence.

In one embodiment, the light from the wafer includes scattered light. In some embodiments, the detection subsystem is configured to collect the light from the wafer at multiple sets of solid angles.

In another embodiment, the processing subsystem is configured to determine a lateral dimension of the defects using the output signals. In an additional embodiment, the processing subsystem is configured to determine a depth of the subsurface defects within the wafer using the output signals. In some embodiments, the processing subsystem is configured to compare the output signals responsive to the light returned from the wafer resulting from the illumination of the wafer with the light at the first wavelength and the output signals responsive to the light returned from the wafer resulting from the illumination of the wafer with the light at the second wavelength as a function of location on the wafer. Each of the embodiments of the system described above may be further configured as described herein.

An additional embodiment relates to a carrier medium that includes program instructions executable on a computer system for performing a method for detecting defects on a wafer. The method includes detecting first defects on the wafer using first output signals responsive to light from the wafer resulting from illumination of the wafer with light at a first wavelength that penetrates into the wafer. The method also includes detecting second defects on the wafer using second output signals responsive to light from the wafer resulting from illumination of the wafer with light at a second wavelength that does not substantially penetrate into the wafer. In addition, the method includes determining if the first and second defects are subsurface defects or surface defects using the first and second output signals generated at approximately the same location on the wafer.

In one embodiment, the first wavelength is a visible wavelength, and the second wavelength is an ultraviolet wavelength. In another embodiment, the light from the wafer resulting from the illumination of the wafer with the light at the first and second wavelengths includes scattered light.

In some embodiments, the method includes determining a lateral dimension of the first or second defects using the first or second output signals, respectively. In another embodiment, the method includes determining a depth of the subsurface defects within the wafer using the first output signals. In a further embodiment, determining if the first and second defects are subsurface defects or surface defects includes comparing the first and second output signals as a function of location on the wafer. The method for detecting defects on the wafer performed by the program instructions may include any other step(s) described herein. Each of the embodiments of the carrier medium described above may be further configured as described herein.

BRIEF DESCRIPTION OF THE DRAWINGS

Other objects and advantages of the invention will become apparent upon reading the following detailed description and upon reference to the accompanying drawings in which.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

A wafer may include one or more layers formed upon a substrate. For example, such layers may include, but are not limited to, a resist, a dielectric material, and a conductive material. Many different types of such layers are known in the art, and the term wafer as used herein is intended to encompass a wafer including all types of such layers.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

Although the embodiments of the methods and systems are described herein with respect to a wafer, it is to be understood that the methods and systems described herein may be used for inspection of any specimen that includes an uppermost layer that is at least partially transparent to a wavelength of light used for the inspection.

As used herein, the term "surface defects" refers to both defects that are located entirely above the upper surface of the wafer (e.g., particles) and defects that are located partially below the upper surface of the wafer (e.g., "surface-breaking" defects such as crystal originated particles (COPs) or pits). In contrast, the term "subsurface defects" as used herein refers to defects that are located entirely below the upper surface of the wafer (e.g., COPs embedded within the wafer or a layer formed on the wafer and voids embedded within a layer formed on the wafer).

Due to significant differences in the depth to which light of different wavelengths penetrates into semiconductor materials, defects on the surface of a wafer or on the upper surface of a multi-layer stack formed on the wafer scatter light differently from defects embedded in the wafer substrate or inside of a multi-layer stack. Unfortunately, when only a single wavelength of light is used for inspection, it can be difficult to discriminate between defect types (e.g., between different types of surface defects) and between surface and subsurface defects. For example, when a bare silicon wafer is illuminated with 488 nm light, a large but deep subsurface defect and a small surface defect may produce similar light scattering signals thereby making discrimination between these defect types substantially difficult if not impossible. If the same defects were to be illuminated with, for example, both 488 nm and 355 nm light, the different penetration depths of the different wavelengths of light (e.g., different by a factor of about 50 in this case) cause very different output signals to be generated by detectors.

The systems and methods described herein exploit these differences in the penetration depths of different wavelengths of light to enable more accurate and quicker classification of defects. Classification of defects is particularly useful for semiconductor materials such as wafers and materials formed on wafers. Discriminating between surface and subsurface defects is particularly important for bare silicon wafers, silicon on insulator (SOI) films, strained silicon films, and dielectric films. The systems and methods described herein can be used to inspect a wafer containing silicon or having a silicon-containing layer formed thereon such as silicon carbide, carbon doped silicon dioxide, SOI, strained silicon, and silicon-containing dielectric films.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 5:
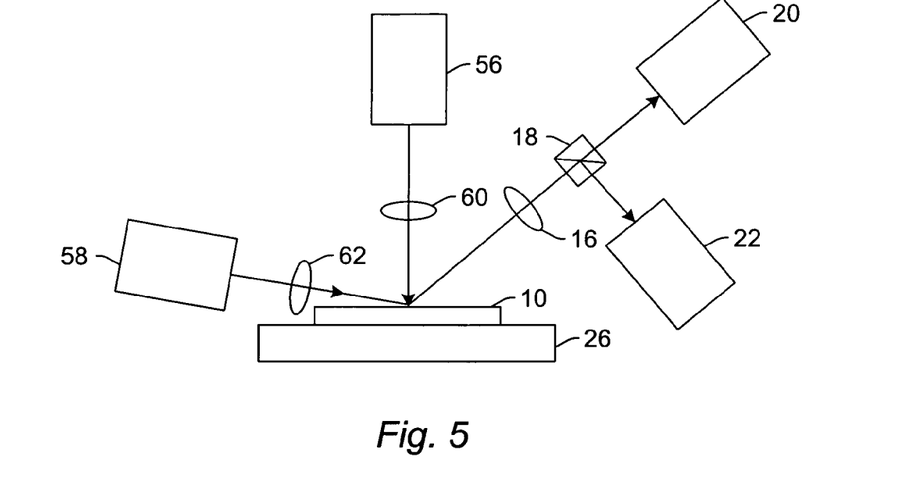
Figure 6:
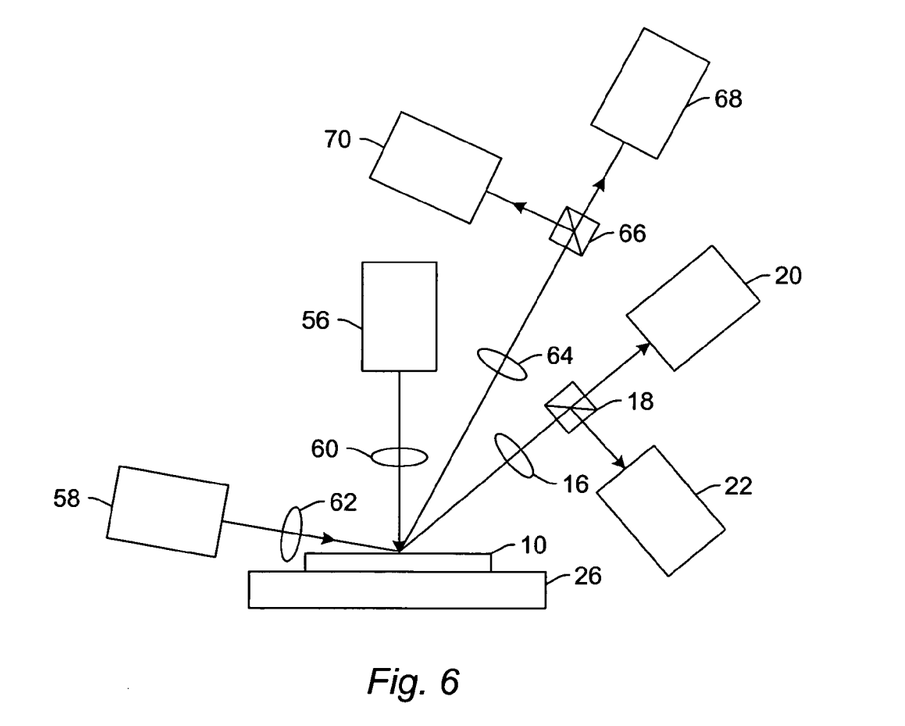
Figure 7:
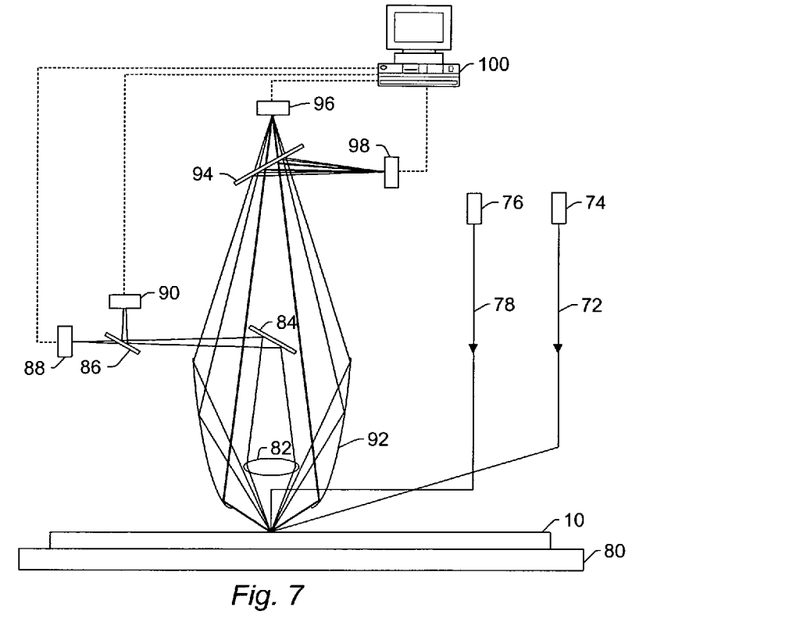

FIGS. 1-7 illustrate various embodiments of a system configured to inspect a wafer. It is noted that FIGS. 1-7 are provided herein to generally illustrate various embodiments of configurations for the system. Obviously, the system configurations described herein may be altered to optimize the performance of the systems as is normally performed when designing a commercial optical system. For instance, FIG. 7 illustrates a more complex configuration of one embodiment of a system configured to inspect a wafer that may have better performance than the systems shown in FIGS. 1-6. However, the configuration of the system shown in FIG. 7 may also be altered and optimized depending on, for example, the desired optical performance of the system and one or more characteristics of the wafers to be inspected by the system. In addition, the systems described herein may be implemented by modifying an existing inspection system (e.g., by adding a laser or lasers to an existing light scattering inspection system). For some such systems, the multi-wavelength inspection and defect classification described herein may be provided as optional functionality of the system (e.g., in addition to other functionality of the system). Alternatively, the systems described herein may be designed "from scratch" to provide multi-wavelength inspection and defect classification.

Figure 1:
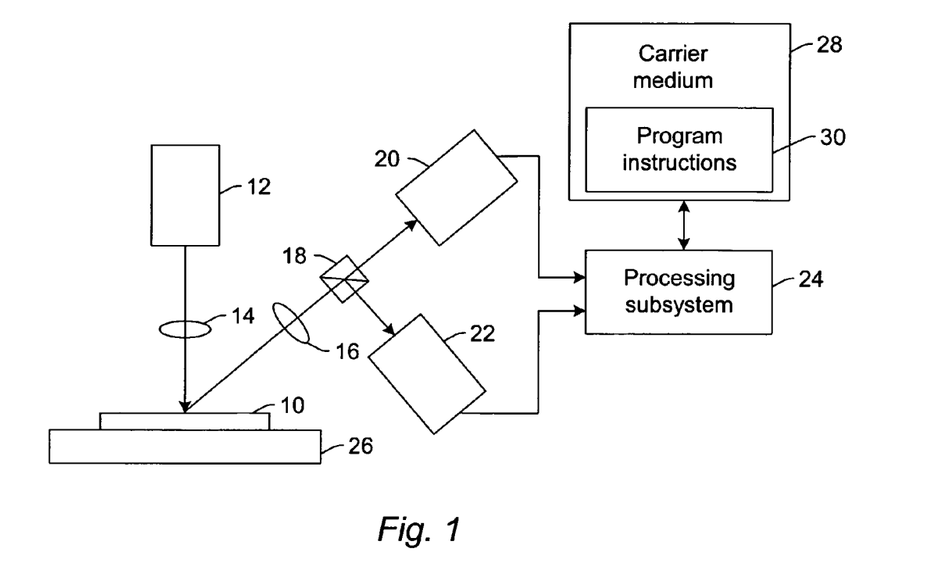
FIGS. 1-7 are schematic diagrams illustrating a cross-sectional view of various embodiments of a system configured to inspect a wafer.

FIG. 1 illustrates one embodiment of a system configured to inspect a wafer. The system includes an illumination subsystem configured to illuminate wafer 10 with light at a first wavelength and light at a second wavelength. The light at the first wavelength penetrates into the wafer, and the light at the second wavelength does not substantially penetrate into the wafer. In this embodiment, the illumination subsystem includes single light source 12. Light source 12 is configured to provide light at both the first and second wavelengths. In one such embodiment, the light source may be a multi-wavelength laser. For example, multiple wavelengths of light may be produced by the same laser if the laser is normally configured to produce light at more than one wavelength. Many commercially available lasers have such configurations. One example of such a laser is a diode-pumped-solid-state (DPSS) ultraviolet laser, which also provides a visible wavelength of light. However, light source 12 may include any other appropriate light source known in the art such as an arc lamp. The illumination subsystem may also include one or more spectral filtering components (not shown) that are configured to select and/or alter the wavelengths of light that are directed to the wafer by the illumination subsystem.

The illumination subsystem also includes objective 14 that is configured to focus the light from light source 12 to the wafer. Although objective 14 is shown in FIG. 1 as a single refractive optical element, it is to be understood that objective 14 may include one or more refractive optical elements and/or one or more reflective optical elements.

As shown in FIG. 1, the illumination subsystem is configured to illuminate the wafer by directing the light at the first and second wavelengths to the wafer at substantially the same angle of incidence. In addition, as shown in FIG. 1, the illumination subsystem is configured to direct the light at the first and second wavelengths to the wafer at a substantially normal angle of incidence. However, in other embodiments (not shown), the illumination subsystem may be configured to direct the light at the first and second wavelengths to the wafer at substantially the same oblique angle of incidence.

The system shown in FIG. 1 also includes a detection subsystem configured to generate output signals responsive to light from the wafer resulting from illumination of the wafer. The light from the wafer may include light scattered from the wafer. In the embodiment shown in FIG. 1, the detection subsystem includes objective 16 that is configured to collect light scattered from the wafer as a result of illumination provided by light source 12 and objective 14. As shown in FIG. 1, objective 16 includes a single refractive optical element. However, objective 16 may include one or more refractive optical elements and/or one or more reflective optical elements. In this embodiment, objective 16 is configured to collect light scattered from the wafer resulting from illumination of the wafer with the first and second wavelengths of light.

As shown in FIG. 1, the detection subsystem includes beam splitter 18. Beam splitter 18 is configured to separate the light collected by objective 16 by wavelength thereby producing two different beams of light. For example, beam splitter 18 may be configured to transmit the first wavelength of light scattered from the wafer and to reflect the second wavelength of light scattered from the wafer. In this manner, the light scattered from the wafer at different wavelengths may be directed to different detectors. Beam splitter 18 may include any appropriate beam splitter known in the art.

For example, as shown in FIG. 1, the detection subsystem includes detectors 20 and 22. Detector 20 is configured to detect light transmitted by beam splitter 18, and detector 22 is configured to detect light reflected by beam splitter 18. In addition, the detection subsystem may include one or more optical components (not shown) such as a focusing or imaging lens disposed in the optical path between beam splitter 18 and each of detectors 20 and 22. Detectors 20 and 22 are configured to generate output signals responsive to the light scattered from the wafer. Detectors 20 and 22 may be any appropriate detectors known in the art such as photomultiplier tubes (PMTs), avalanche photodiodes (APDs), charge coupled devices (CCDs), and time delay integration (TDI) cameras to name just a few. In addition, detectors 20 and 22 may be similarly or differently configured.

The system shown in FIG. 1 is configured to perform inspection at multiple wavelengths (i.e., at least the first and second wavelengths). The illumination subsystem shown in FIG. 1 may be configured to illuminate the wafer with the light at the first and second wavelengths simultaneously, and the detection subsystem shown in FIG. 1 may be configured to generate output signals responsive to the light of both wavelengths scattered from the wafer substantially simultaneously. Therefore, the system shown in FIG. 1 may be configured to scan and inspect the wafer with both wavelengths of light simultaneously. In this manner, inspection of the wafer at the multiple wavelengths may be performed in a single scan of the wafer. When multiple wavelengths of light are incident on the wafer simultaneously as described above, wavelength filtering may be performed at the detector(s) to provide separate detection of each wavelength of light thereby providing more accurate defect detection and discrimination of the defects. For example, the detection subsystem may include one or more spectral filtering components disposed between beam splitter 18 and each of the detectors.

However, in other embodiments, the illumination subsystem of the system shown in FIG. 1 may be configured to illuminate the wafer with light at the first and second wavelengths sequentially. In this manner, inspection of the wafer at the multiple wavelengths may be performed in different scans of the wafer. In particular, inspection can be performed sequentially in multiple physical scans of the wafer, one at each wavelength. In one such embodiment, the illumination subsystem may include one or more filters (not shown), and the wavelength of light that is directed to the wafer may be altered between scans of the wafer by altering the filter that is positioned in the optical path of the illumination subsystem. However, the illumination subsystem may be configured to sequentially illuminate the wafer with different wavelengths of light in any other suitable manner known in the art. In such embodiments, the detection subsystem of the system shown in FIG. 1 is configured to detect the light scattered from the wafer at the first and second wavelengths sequentially. In one such embodiment, the detection subsystem may include only one detector that is used to detect scattered light at the different wavelengths sequentially. In this manner, the detection subsystem may not include beam splitter 18 and detector 22, and detector 20 may be used to detect the light scattered from the wafer at the different wavelengths sequentially.

Detectors 20 and 22 may be coupled to processing subsystem 24, as shown in FIG. 1. Processing subsystem 24 may be coupled to detectors 20 and 22 such that the processing subsystem can receive the output signals generated by the detectors. For example, processing subsystem 24 may be coupled to each of the detectors by a transmission medium (not shown) or an electronic component (not shown) interposed between each of the detectors and the processing subsystem. The transmission media and the electronic components may include any suitable such media and components known in the art.

Processing subsystem 24 is configured to detect defects on the wafer using the output signals. For example, processing subsystem 24 may be configured to detect the defects by comparing the output signals to a threshold. If the output signals have a value higher than the threshold, then the output signals may identified by the processing subsystem as corresponding to the presence of a defect on the wafer. However, processing subsystem 24 may be configured to use any method and/or algorithm to detect defects on the wafer using the output signals. In addition, the processing subsystem is configured to detect defects on the wafer by separately analyzing the output signals that are responsive to light scattered from the wafer at the different wavelengths. In this manner, the processing subsystem is configured to detect one set of defects on the wafer using the output signals responsive to light scattered from the wafer at the first wavelength and another set of defects on the wafer using the output signals responsive to light scattered from the wafer at the second wavelength. The processing subsystem may be configured to detect the different sets of defects in a similar or different manner (e.g., with different threshold values).

Processing subsystem 24 is further configured to determine if the defects are subsurface defects or surface defects using the output signals. The processing subsystem may determine if the defects are subsurface defects or surface defects using the output signals generated by detectors 20 and 22 in combination. In particular, substantial differences in the penetration depth of different wavelengths of light into the material of interest cause substantially different scattering signals to be produced at the various wavelengths (e.g., at the various detectors). In this manner, the processing subsystem may be configured to compare the output signals generated by detecting scattered light at the first and second wavelengths as a function of location on the wafer.

Analyzing the output signals produced at the different wavelengths may include, for example, comparing the magnitude of the output signals. For example, in one embodiment, the processing subsystem is configured to compare the output signals responsive to the light returned from the wafer resulting from the illumination of the wafer with the light at the first wavelength and the output signals responsive to the light returned from the wafer resulting from the illumination of the wafer with the light at the second wavelength. The processing subsystem may be configured to compare the different output signals as a function of location on the wafer. In other words, for each defect detected at any wavelength, the different output signals produced for the multiple wavelengths at the location of the defect may be compared in order to classify the defect as a subsurface or surface defect. In this manner, the output signals generated at the first wavelength and the second wavelength at a single location on the wafer corresponding to a defect detected at one or both of the wavelengths may be compared. Instead of comparing the output signals, the output signals may be used to determine a value of a function of the output signals such as a ratio, a difference, or some more complicated algorithmic combination of the output signals, either before or after calibration with respect to standard defects such as polystyrene latex (PSL) spheres.

In one such embodiment, since the first wavelength penetrates into the wafer and the second wavelength does not substantially penetrate into the wafer, the magnitude of the light at the different wavelengths scattered by a defect will vary depending on the position of the defect with respect to the upper surface of the wafer. In other words, the magnitude of the light scattered by a defect at the different wavelengths will vary depending on the position of the defect with respect to the depth to which the different wavelengths penetrate into the wafer. In this manner, the first and second wavelengths may be selected to reveal the differences between scattering from surface defects and subsurface defects at the different wavelengths. Obviously, since the first wavelength is selected such that light at this wavelength penetrates into the wafer and the second wavelength is selected such that light at this wavelength does not substantially penetrate into the wafer, the first and second wavelengths may be selected based on one or more characteristics of the material or materials to be inspected such as absorption characteristics and thickness.

In one such example, a silicon wafer or a silicon-containing layer on a wafer may be inspected by the systems described herein. The absorption coefficient of silicon varies greatly throughout the visible and ultraviolet spectrum. In particular, longer wavelengths of light penetrate much farther into silicon than shorter wavelengths of light. In this manner, for a system configured to inspect a wafer, in one embodiment, the first wavelength is a visible wavelength, and the second wavelength is an ultraviolet wavelength. In one such embodiment, the first wavelength may be about 488 nm, and the second wavelength may be about 355 nm. The ratio of the penetration depths of light at 488 nm and 355 nm is a factor of about 50 (e.g., light at about 488 nm will penetrate about 500 nm into the wafer, and light at about 355 nm will penetrate about 10 nm into the wafer).

A surface defect will scatter light at both wavelengths, albeit at different amounts. However, a subsurface defect will scatter light much differently. For instance, for a subsurface defect about 100 nm in diameter and submerged about 200 nm into a silicon substrate, light at a wavelength of 488 nm will penetrate through the silicon substrate to the defect and scatter off of the defect. Some of the scattered light will return to the surface and can be collected and detected as described herein. The signal responsive to this scattered light will be weaker than that from an equivalently-sized surface defect but will be detectable if the defect has a sufficiently large diameter. However, the penetration depth of 355 nm light is substantially small (e.g., about 10 nm) such that virtually no light can impinge upon and be scattered from the defect. Therefore, the output signal corresponding to light at 355 nm scattered from the subsurface defect is effectively zero. As such, 488 nm scattered and detected light will reveal the defect, but 355 nm scattered and detected light will not. This discrepancy in the output signals of the scattered light detected at the different wavelengths thereby provides a way to detect subsurface defects and to distinguish them from surface defects.

As described above, the output signals for different wavelengths of scattered light may be compared at locations on the wafer at which at least one wavelength of scattered light indicated the presence of a defect. In some other embodiments, the positions of the defects detected at both wavelengths may be compared. For instance, wafer maps that each show the defects detected at one wavelength may be overlaid to illustrate positions on the wafer at which defects were detected by one or more of the wavelengths. In this manner, the processing subsystem may be configured to compare the first set of defects to the second set of defects to determine if defects of the first and second sets are located at approximately the same position on the wafer. When only one wavelength of light indicates the presence of a defect, the defect may be assigned a classification based on the wavelength at which the defect was detected. In particular, defects detected at only the penetrating wavelength may be classified as subsurface defects, and defects detected at only the substantially non-penetrating wavelength may be classified as surface defects. For a defect of the first set that is located at approximately the same position on the wafer as a defect of the second set, the processing subsystem may analyze the output signals corresponding to these defects as described further above to determine if the defects of the first and second sets represent a subsurface defect or a surface defect.

In one embodiment, the processing subsystem is configured to determine a depth of the subsurface defects within the wafer using the output signals. For example, the subsurface defects may be classified by depth in the wafer using a comparison of the output signals responsive to the light scattered at the first and second wavelengths. In addition, depending on the signal strength and number of wavelengths incident on the wafer and detected by the system, it may be possible to determine the depth of the subsurface defects.

For example, in another embodiment, the system may be configured to illuminate the wafer with more than two wavelengths of light, one of which does not substantially penetrate into the wafer and two or more of which penetrate into the wafer but to different depths. In addition, the system may be configured to generate output signals responsive to light scattered from the wafer at each of the more than two penetrating wavelengths of light. In this manner, the output signals corresponding to the light scattered at the two or more wavelengths that penetrate into the wafer may be used in combination to determine the depth at which the defect is located within the wafer. For example, a defect that is located closer to the shallower penetration depth of one wavelength that penetrates into the wafer may scatter approximately the same amount of light at both of the penetrating wavelengths. However, a defect that is located closer to the deeper penetration depth of the other wavelength that penetrates into the wafer may scatter almost no light at the less penetrating wavelength and at least some light at the more penetrating wavelength. Therefore, the output signals corresponding to the light scattered at the penetrating wavelengths generated at approximately the same position on the wafer corresponding to a position of a defect detected at any of the penetrating wavelengths may be used in combination to determine an approximate depth of the defect within the wafer.

It is noted that the system may be configured to inspect the wafer using any suitable number of penetrating wavelengths and any suitable number of substantially non-penetrating wavelengths. Additional wavelength capability may be provided, for example, by adding light source(s) to the system, replacing the single light source with a different single light source, adding beam splitters to the illumination path, adding beam splitters and detectors to the detection subsystem, etc. It is also noted that the system configuration may increase in complexity as the number of wavelengths increases. Therefore, the number of wavelengths at which the system is configured to generate output signals may be selected based on the wafer characteristics (e.g., absorption characteristics) and may be selected to provide only as much information needed to accurately detect and discriminate between the defect types of interest.

In another embodiment, the processing subsystem is configured to determine a lateral dimension (e.g., diameter) of the defects using the output signals. The processing subsystem may be configured to determine a lateral dimension of both subsurface defects and surface defects. The output signals that are used to determine the lateral dimension of the subsurface defects may include only the output signals corresponding to the light scattered at the penetrating wavelength. The output signals that are used to determine the lateral dimension of the surface defects may include only the output signals corresponding to the light scattered at the substantially non-penetrating wavelength. In this manner, the lateral dimension may be determined from the light that has a penetration depth closest to the position of the defects in the wafers, which may increase the accuracy with which the lateral dimension of the defects can be determined. In another embodiment, the defects may be classified by size using a comparison of the output signals generated at both wavelengths.

The output of the analysis performed by the processing subsystem may, therefore, include a determination of whether a defect lies on the surface of the wafer or is embedded in the wafer and optionally the size of the defect (e.g., with respect to some calibration standard) and/or, if the defect is a subsurface defect, the depth of the defect within the wafer.

Processing subsystem 24 may take various forms, including a personal computer system, mainframe computer system, workstation, image computer, parallel processor, or any other suitable device known in the art. In general, the term "computer system" may be broadly defined to encompass any device having one or more processing subsystems, which executes instructions from a memory medium.

The system shown in FIG. 1 may also include carrier medium 28. Program instructions for implementing methods such as those described herein may be transmitted over or stored on the carrier medium. In particular, carrier medium 28 includes program instructions 30 executable on processing subsystem 24 for performing one or more steps of the methods described herein. For example, in one embodiment, carrier medium 28 includes program instructions executable on a computer system such as processing subsystem 24 for performing a method for detecting defects on wafer 10. In addition, the carrier medium may include program instructions executable on a computer system of any other inspection system that is or can be configured as described herein.

The method performed by the program instructions includes detecting first defects on the wafer using first output signals responsive to light from wafer 10 resulting from illumination of the wafer with light at a first wavelength that penetrates into the wafer. Detecting the first defects may be performed as described herein. In one such embodiment, the first output signals may be generated by detector 20 or 22. As described further above, the first wavelength may be a visible wavelength. The light from the wafer resulting from illumination of the wafer with light at the first wavelength may include scattered light.

The method also includes detecting second defects on the wafer using second output signals responsive to light from the wafer resulting from illumination of the wafer with light at a second wavelength that does not substantially penetrate into the wafer. Detecting the second defects on the wafer may be performed as described herein. In one embodiment, if the first output signals are generated by detector 20, then the second output signals are generated by detector 22 or vice versa. The second wavelength may be an ultraviolet wavelength. The light from the wafer resulting from illumination of the wafer with light at the second wavelength may include scattered light.

In addition, the method includes determining if the first and second defects are subsurface defects or surface defects using the first and second output signals generated at approximately the same location on the wafer in combination. Determining if the first and second defects are subsurface defects or surface defects may be performed as described further herein. For example, in one embodiment, determining if the first and second defects are subsurface defects or surface defects includes comparing the first and second output signals as a function of location on the wafer.

The method performed by the program instructions may include any other step(s) described herein. For example, in one embodiment, the method includes determining a lateral dimension of the first or second defects using the first or second output signals, respectively. In another embodiment, the method includes determining a depth of the subsurface defects within the wafer using the first output signals.

The carrier medium may be a transmission medium such as a wire, cable, or wireless transmission link. The carrier medium may also be a storage medium such as a read-only memory, a random access memory, a magnetic or image acquisition disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

The system may also include stage 26 on which wafer 10 may be disposed during inspection. Stage 26 may include any suitable mechanical or robotic assembly known in the art. Scanning of illumination across the wafer may be performed by moving the illumination and detection subsystems in conjunction while the wafer is stationary, moving (e.g., translating and/or rotating) the wafer while the illumination and detection subsystems are stationary, or moving the illumination and detection subsystems and the wafer simultaneously.

The system shown in FIG. 1 may be further configured as described herein (e.g., according to any other embodiments described herein).

As described further above, the illumination subsystem of the system of FIG. 1 is configured to direct light at the first and second wavelengths to the wafer at substantially the same angle of incidence. In other embodiments, the illumination subsystem is configured to illuminate the wafer by directing the light at the first and second wavelengths to the wafer at different angles of incidence.

Figure 2:
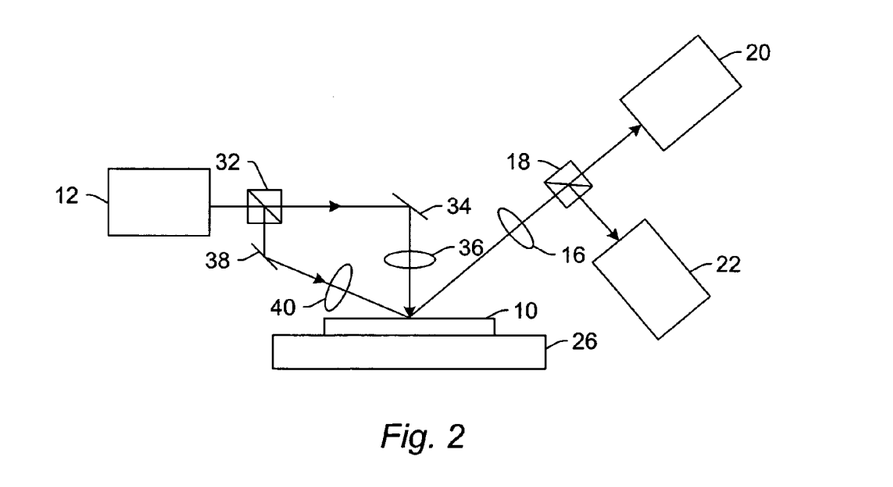

One embodiment of a system that includes such an illumination subsystem is illustrated in FIG. 2. For example, as shown in FIG. 2, the illumination subsystem includes single light source 12, which may be configured as described above. The illumination subsystem also includes beam splitter 32. The illumination subsystem is configured such that light from light source 12 is directed to beam splitter 32. Beam splitter 32 is configured to separate the light from light source 12 into two different beams of light by wavelength. For example, beam splitter 32 may be configured to transmit light at the first wavelength and to reflect light at the second wavelength. Beam splitter 32 may include any suitable optical component known in the art.

Light transmitted by beam splitter 32 is directed to reflective optical component 34 of the illumination subsystem. Reflective optical component 34 is configured to direct the light that is transmitted by beam splitter 32 to objective 36, which focuses the light onto wafer 10. As shown in FIG. 2, reflective optical component 34 and objective 36 are configured such that the light that is transmitted by beam splitter 32 is directed to wafer 10 at a substantially normal angle of incidence. In this manner, light at the first wavelength that penetrates into the wafer may be directed to the wafer at a substantially normal angle of incidence. Reflective optical component 34 may include any appropriate reflective optical component known in the art such as a flat mirror. Objective 36 may be further configured as described herein.

Light reflected by beam splitter 32 is directed to reflective optical component 38 of the illumination subsystem. Reflective optical component 38 is configured to direct the light that is reflected by beam splitter 32 to objective 40, which focuses the light onto wafer 10. As shown in FIG. 2, reflective optical component 34 and objective 40 are configured such that the light that is reflected by beam splitter 32 is directed to wafer 10 at an oblique angle of incidence. In this manner, light at the second wavelength that does not substantially penetrate into the wafer may be directed to the wafer at an oblique angle of incidence. The oblique angle at which the light at the second wavelength is directed to the wafer may include any suitable oblique angle known in the art. In addition, the oblique angle may vary and be selected based on, for example, the second wavelength and one or more characteristics of the wafer. Reflective optical component 38 may include any appropriate reflective optical component known in the art. Objective 40 may be further configured as described herein.

The system shown in FIG. 2 may be further configured as described herein. For example, the system shown in FIG. 2 includes a detection subsystem and a processing subsystem (not shown in FIG. 2) that may be configured as described above. In addition, the illumination subsystem shown in FIG. 2 may be configured as described further above such that the light at the first and second wavelengths is directed to the wafer sequentially or simultaneously. Furthermore, the detection subsystem shown in FIG. 2 may be configured as described herein such that the light at the first and second wavelengths scattered from the wafer is detected sequentially or simultaneously.

Figure 3:
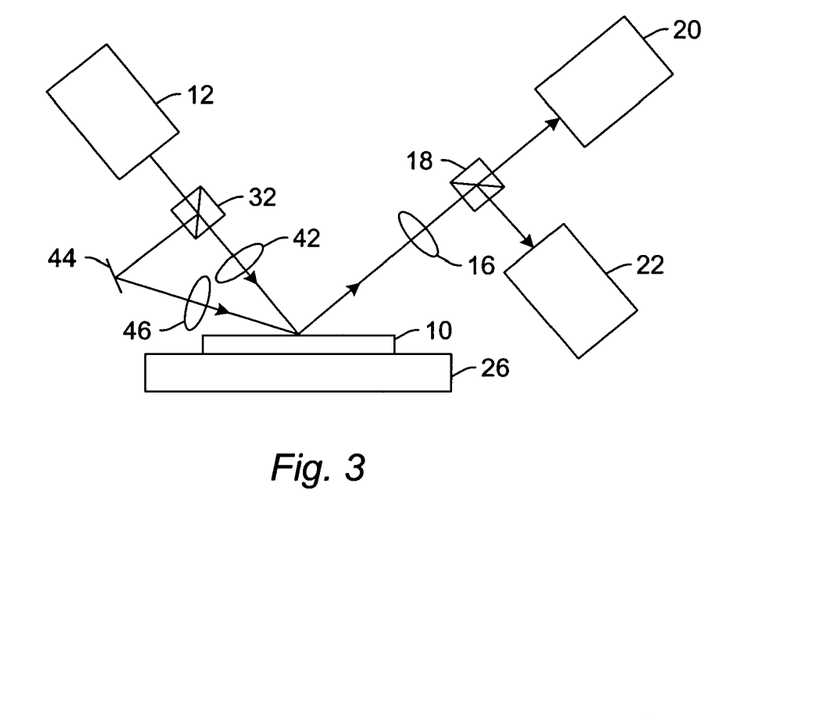

Another embodiment of a system that includes an illumination subsystem configured to direct light at the first and second wavelengths to the wafer at different angles of incidence is illustrated in FIG. 3. Like the systems shown in FIGS. 1 and 2, the illumination subsystem of the system shown in FIG. 3 includes single light source 12. However, unlike the illumination subsystem shown in FIG. 2, in this embodiment, the light at the first and second wavelengths is directed to the wafer at two different oblique angles of incidence.

As shown in FIG. 3, light from light source 12 is separated into two different beams of light having two different wavelengths by beam splitter 32 of the illumination subsystem. Beam splitter 32 may be further configured as described herein. In one embodiment, light of the first wavelength may be transmitted by beam splitter 32. The illumination subsystem may include objective 42 that is configured to focus the light transmitted by the beam splitter onto wafer 10. Objective 42 may be further configured as described herein. As shown in FIG. 3, beam splitter 32 and objective 42 are configured such that the light at the first wavelength is directed to the wafer at an oblique angle of incidence.

Light of the second wavelength may be reflected by beam splitter 32. The illumination subsystem may also include reflective optical component 44 and objective 46, which in combination are configured to direct the light at the second wavelength to the wafer at an oblique angle of incidence. Reflective optical component 44 and objective 46 may be further configured as described herein. The light at the first and second wavelengths is directed to the wafer at different oblique angles of incidence. The different oblique angles of incidence may vary and may be selected based on the first and second wavelengths of light and one or more characteristics of the wafer.

The system shown in FIG. 3 may be further configured as described herein. For example, the system shown in FIG. 3 includes a detection subsystem and a processing subsystem (not shown in FIG. 3) that may be configured as described above. In addition, the illumination subsystem shown in FIG. 3 may be configured as described further above such that the light at the first and second wavelengths is directed to the wafer sequentially or simultaneously. Furthermore, the detection subsystem shown in FIG. 3 may be configured such that the light at the first and second wavelengths scattered from the wafer is detected sequentially or simultaneously.

As described further above, the illumination subsystem of the systems described herein may include a single light source, which generates light at the first and second wavelengths that is directed to the wafer at substantially the same angle of incidence or different angles of incidence. In other embodiments, the illumination subsystem includes more than one light source. One of the more than one light source is configured to generate the light at the first wavelength. Another of the more than one light source is configured to generate the light at the second wavelength.

Figure 4:
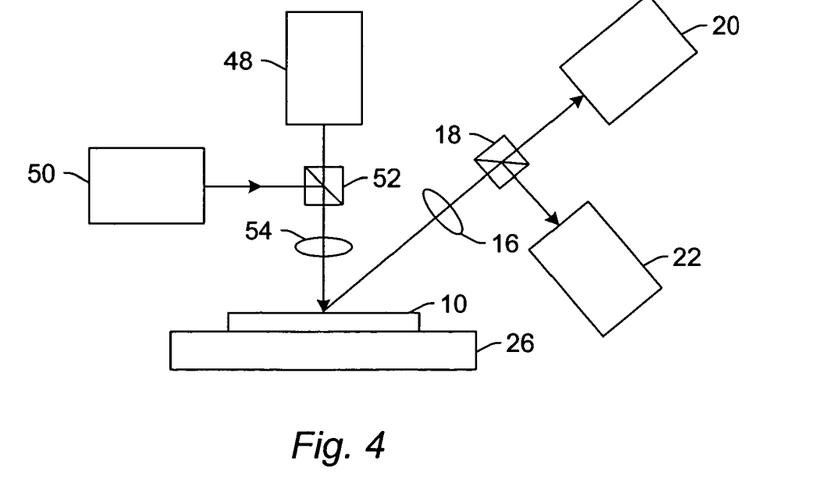

One embodiment of a system that includes such an illumination subsystem is shown in FIG. 4. The illumination subsystem of this embodiment includes light sources 48 and 50. One of light sources 48 and 50 is configured to generate the light at the first wavelength, and the other of light sources 48 and 50 is configured to generate the light at the second wavelength. Light sources 48 and 50 may include any suitable light sources known in the art such as single wavelength lasers and light emitting diodes. In addition, the light sources may be selected based on the first and second wavelengths, which may be selected as described further herein.

As shown in FIG. 4, light from light sources 48 and 50 may be combined into a single illumination path by beam splitter 52 of the illumination subsystem, which is configured to transmit light from light source 48 and to reflect light from light source 50. In this manner, light at the first and second wavelengths is directed to wafer 10 at substantially the same angle of incidence. As shown in FIG. 4, the light at the first and second wavelengths is directed to the wafer at a substantially normal angle of incidence. However, the light at the first and second wavelengths may be directed to the wafer at an oblique angle of incidence. Light transmitted and reflected by beam splitter 52 may be focused to wafer 10 by objective 54 of the illumination subsystem. Beam splitter 52 and objective 54 may be further configured as described herein.

The system shown in FIG. 4 may be further configured as described herein. For example, the system shown in FIG. 4 includes a detection subsystem and a processing subsystem (not shown in FIG. 4) that may be configured as described above. In addition, the illumination subsystem shown in FIG. 4 may be configured as described further above such that the light at the first and second wavelengths is directed to the wafer sequentially or simultaneously. Furthermore, the detection subsystem shown in FIG. 4 may be configured such that the light at the first and second wavelengths scattered from the wafer is detected sequentially or simultaneously.

As described further above, the illumination subsystem may include more than one light source, and the light from each of the light sources may be directed to the wafer at substantially the same angle of incidence. In alternative embodiments, the illumination subsystem includes more than one light source, one of which is configured to generate the light at the first wavelength and another of which is configured to generate the light at the second wavelength, and the illumination subsystem is configured to illuminate the wafer by directing the light at the first and second wavelengths to the wafer at different angles of incidence.

One embodiment of a system that includes such an illumination subsystem is illustrated in FIG. 5. The illumination subsystem of this embodiment includes light sources 56 and 58. One of light sources 56 and 58 is configured to generate the light at the first wavelength, and the other of light sources 56 and 58 is configured to generate the light at the second wavelength. Light sources 56 and 58 may include any suitable light sources known in the art such as single wavelength lasers. In addition, the light sources may be selected based on the first and second wavelengths, which may be selected as described further herein.

As shown in FIG. 5, light from light source 56 is focused by objective 60 to wafer 10 at a substantially normal angle of incidence. In one such embodiment, light source 56 is configured to generate light at the first wavelength that penetrates into wafer 10. Light from light source 58 is focused by objective 62 to wafer 10 at an oblique angle of incidence. In one such embodiment, light source 58 is configured to generate light at the second wavelength that does not substantially penetrate into the wafer. The oblique angle of incidence may be selected as described herein. Objectives 60 and 62 may be configured as described herein.

The system shown in FIG. 5 may be further configured as described herein. For example, the system shown in FIG. 5 includes a detection subsystem and a processing subsystem (not shown in FIG. 5) that may be configured as described herein. In addition, the illumination subsystem shown in FIG. 5 may be configured as described further above such that the light at the first and second wavelengths is directed to the wafer sequentially or simultaneously. Furthermore, the detection subsystem shown in FIG. 5 may be configured such that the light at the first and second wavelengths scattered from the wafer is detected sequentially or simultaneously.

In other embodiments, the illumination subsystem may include more than one light source, which may be configured as described herein. However, unlike the illumination subsystem shown in FIG. 5, the illumination subsystem may be configured to illuminate the wafer by directing the light from more than one light source to the wafer at different oblique angles of incidence. In some such embodiments, the illumination subsystem may also be configured to illuminate the wafer by directing the light from the more than one light source to the wafer at different azimuthal angles. Such embodiments may be further configured as described herein.

As described above, the detection subsystem of the system embodiments may be configured to collect the light from the wafer at a single set of solid angles (e.g., as defined by the position and characteristics of objective 16). However, in other embodiments, the detection subsystem may be configured to collect the light from the wafer at multiple sets of solid angles. In this manner, the scattered light may be collected into multiple sets of solid angles, and at each set, the light may be detected at each wavelength individually.

One embodiment of a system that includes such a detection subsystem is shown in FIG. 6. The system shown in FIG. 6 includes an illumination subsystem that is configured as shown in FIG. 5 described further above. However, it is to be understood that the system shown in FIG. 6 may include any of the illumination subsystem embodiments described herein. As further shown in FIG. 6, the system includes a detection subsystem that includes objective 16, beam splitter 18, and detectors 20 and 22, each of which may be configured as described herein. Detectors 20 and 22 are configured to detect light scattered from the wafer at more than one wavelength and at one set of solid angles as defined by objective 16. The detection subsystem also includes objective 64, beam splitter 66, and detectors 68 and 70, each of which may be configured as described herein. As shown in FIG. 6, objective 64 is configured to collect light scattered by the wafer at a set of solid angles that is different than the set of solid angles at which objective 16 collects light scattered by the wafer. Objectives 16 and 64 may also be configured to collect light scattered from the wafer at different sets of solid angles that are different in polar angle and/or azimuthal angle within the collection space. In this manner, the detection subsystem of the system shown in FIG. 6 is configured to collect and detect the light scattered from the wafer at multiple sets of solid angles. The light at the first and second wavelengths scattered by the wafer may be detected at both sets of the solid angles.

In such embodiments, the output signals produced by the detection subsystem at both sets of solid angles may be processed as described further herein to detect defects on the wafer and to determine if the defects are subsurface defects or surface defects. For instance, multiple scans of the wafer at different wavelengths may be performed by the system shown in FIG. 6 simultaneously or sequentially. After the scans have been completed, the output signals may be processed, and for each defect found at any wavelength, a comparison is made of the signals produced for the multiple wavelengths and the multiple sets of collected solid angles in order to classify the defect.

The system shown in FIG. 6 may be further configured as described herein. For example, the system shown in FIG. 6 includes a processing subsystem (not shown in FIG. 6) that may be configured as described above. In addition, the illumination subsystem shown in FIG. 6 may be configured as described above such that the light at the first and second wavelengths is directed to the wafer sequentially or simultaneously. Furthermore, the detection subsystem shown in FIG. 6 may be configured such that the light at the first and second wavelengths scattered from the wafer is detected sequentially or simultaneously.

In one particular embodiment of the system shown in FIG. 6, the first wavelength of light that penetrates into the wafer may be directed to the wafer at a normal angle of incidence. The first wavelength may be visible light at a wavelength of, for example, 488 nm or 532 nm. In such an embodiment, the second wavelength of light that does not substantially penetrate into the wafer may be directed to the wafer at an oblique angle of incidence. The second wavelength may be ultraviolet light at a wavelength of, for example, 355 nm. The oblique angle of incidence may be, for example, about 70 degrees from normal. In addition, in such embodiments, the detection subsystem may be configured as described further herein to maintain wavelength separation of the two sets of solid angles for each wavelength collected during detection.

Obviously, the above-described configuration is only one of the many different optical configurations encompassed by the embodiments described herein, and any other suitable optical configuration may be employed in the embodiments described herein. In addition, although in this example, wavelengths of 488 nm, 532 nm, and 355 nm are provided as examples of the first and second wavelengths, a large variety of wavelengths may obviously be used in the systems described herein. In fact, different wavelengths may be better suited to one material than another. As described above, therefore, the first and second (and any other) wavelengths used for inspection may be selected based on one or more characteristics of the wafer such as the absorption characteristics and thickness of the materials formed on the wafer.

Another embodiment of a system that is configured to inspect a wafer is illustrated in FIG. 7. The system shown in FIG. 7 is configured for unpatterned wafer inspection and is based on the SP1-TBI system, which is commercially available from KLA-Tencor, San Jose, Calif. This inspection system is described in more detail in U.S. Pat. No. 6,538,730 to Vaez-Iravani et al., which is incorporated by reference as if fully set forth herein. The system shown in FIG. 7 may be further configured as described in this patent for patterned and unpatterned wafer inspection. For the sake of clarity, some of the components and details of the system have been omitted from FIG. 7 and the corresponding description presented herein. In addition, U.S. Pat. No. 6,538,730 is related to U.S. Pat. No. 6,201,601 to Vaez-Iravani et al. and U.S. Pat. No. 6,271,916 to Marxer et al., which are also incorporated by reference as if fully set forth herein. The system shown in FIG. 7 may be further configured as described in these patents.

The system shown in FIG. 7 includes an illumination subsystem. The illumination subsystem may be configured to generate light 72. For instance, the illumination subsystem may include light source 74, which is configured to generate light 72. Light 72 may be light at the second wavelength that does not substantially penetrate into the wafer. The illumination subsystem is configured to direct light 72 to wafer 10 at an oblique angle of incidence. The illumination subsystem may include a number of optical components (not shown) positioned in a path of light 72 such as folding mirror(s), beam splitter(s), polarizing component(s), filter(s), and lenses. The oblique angle of incidence may vary depending on, for example, the characteristics of the light and the characteristics of the wafer. One suitable angle of incidence may be about 70° from normal to the upper surface of the wafer.

The illumination subsystem also includes light source 76. Light source 76 is configured to generate light 78, which is directed by the illumination subsystem to wafer 10 at a substantially normal angle of incidence. Light 78 may be light at the first wavelength that penetrates into the wafer. The illumination subsystem may include a number of optical components (not shown) positioned in the path of light 78. These optical components may include any of those described above.

Light sources 74 and 76 may include any suitable light sources known in the art such as lasers. In a different embodiment, the system may include a single light source (not shown) that is used to provide light for both oblique and normal illumination as described further above. For example, as described further above, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The different wavelengths may include the first and second wavelengths described herein. The illumination subsystem may include any other suitable combination of a single light source and beam multiplier(s) known in the art.

Wafer 10 is supported on stage 80, which may be rotated and translated such that light 72 and 78 illuminates an area or spot on the wafer that moves in a spiral path. Alternatively, light 72 and 78 may be scanned over the wafer in any manner known in the art to trace the spiral path or another type of scan path across the wafer.

Illumination of the wafer will cause scattering of the light from the wafer. In addition, both oblique incidence light and normal incidence light may be scattered from the wafer. The system shown in FIG. 7 includes a detection subsystem that is configured to collect light scattered from the wafer and to generate output signals responsive to light from the wafer resulting from illumination of the wafer. The output signals can be used to detect defects on the wafer as described further herein.

The detection subsystem includes lens collector 82, mirror 84, beam splitter 86, and detectors 88 and 90, which form a "narrow" channel of the detection subsystem. In other words, light scattered from the illuminated area on the wafer along directions relatively close to normal to the surface of the wafer is collected and focused by lens collector 82. In this manner, lens collector 82 collects light scattered from the wafer at relatively "narrow" scattering angles. Lens collector 82 directs the collected light to mirror 84, which directs the light to beam splitter 86. Beam splitter 86 is configured to direct one portion of the light to detector 88 and the other portion of the light to detector 90. One detector may be used to detect light scattered at relatively narrow angles due to illumination by the normal incidence beam, and the other detector may be used to detect light scattered at relatively narrow angles due to illumination by the oblique incidence beam. Detectors 88 and 90 may include any suitable detectors known in the art (e.g., PMTs). In addition, detectors 88 and 90 may be similarly or differently configured. The narrow channel portion of the detection subsystem may include any other optical components (not shown) known in the art. For example, one or more spectral filtering components (e.g., bandpass filters) may be placed in the path of the collected light between beam splitter 86 and each of detectors 88 and 90. In addition, a spatial filter may be included in the narrow channel portion of the detection subsystem to prevent the specular reflection of the normal incidence beam from reaching detectors 88 and 90.

The detection subsystem also includes ellipsoidal mirror 92, beam splitter 94, and detectors 96 and 98, which form a "wide channel" of the detection subsystem. In other words, light scattered from the illuminated area on the wafer along directions relatively far from normal to the surface of the wafer is collected and focused by ellipsoidal mirror 92. In this manner, ellipsoidal mirror 92 collects light scattered from the wafer at relatively "wide" scattering angles. Ellipsoidal mirror 92 directs the collected light to beam splitter 94. Beam splitter 94 is configured to direct one portion of the light to detector 96 and the other portion of the light to detector 98. One detector may be used to detect light scattered at relatively wide angles due to illumination by the normal incidence beam, and the other detector may be used to detect light scattered at relatively wide angles due to illumination by the oblique incidence beam. Detectors 96 and 98 may include any suitable detectors known in the art (e.g., PMTs). In addition, detectors 96 and 98 may be similarly or differently configured. The wide channel portion of the detection subsystem may include any other optical components (not shown) known in the art. For example, one or more spectral filtering components (e.g., bandpass filters) may be placed in the path of the collected light between beam splitter 94 and each of detectors 96 and 98.

Detectors 88, 90, 96, and 98 are configured to generate output signals responsive to the scattered light. Processing subsystem 100 is coupled to detectors 88, 90, 96, and 98 by transmission media as shown by the dotted lines in FIG. 7. The transmission media may include any suitable transmission media known in the art. In addition, one or more additional components (not shown) may be interposed between each of the detectors and the processing subsystem such as analog-to-digital converters. In this manner, output signals generated by the detectors can be sent to the processing subsystem. The processing subsystem is configured to detect defects on the wafer using the output signals as described further herein. In addition, the processing subsystem is configured to determine if the defects are subsurface defects or surface defects using the output signals as described further herein. The system shown in FIG. 7 may be further configured as described herein.

The embodiments of the systems described herein have a number of advantages over other currently available inspection systems. For instance, the systems described herein provide relatively quick feedback to the user about additional properties of the defects such as surface/subsurface classification, depth classification, and more accurate size than that which can be determined using a single wavelength for inspection. In addition, this additional information can be provided without performing a separate review of the defects on a relatively slow defect review tool such as a scanning electron microscope (SEM) or atomic force microscope (AFM). Furthermore, the systems described herein can be used to detect and classify defects on materials such as SOI and strained silicon, which are becoming more commonly used in semiconductor manufacturing. Therefore, classification of defects on these materials will also become more important.

In some embodiments, the systems described herein may be configured as "stand alone tools" or tools that are not physically coupled to a process tool. However, such a system may be coupled to the process tool (not shown) by a transmission medium, which may include wired and wireless portions. The process tool may include any process tool known in the art such as a lithography tool, an etch tool, a deposition tool, a polishing tool, a plating tool, a cleaning tool, or an ion implantation tool. The process tool may be configured as a cluster tool or a number of process modules coupled by a common handler.

Figure 8:
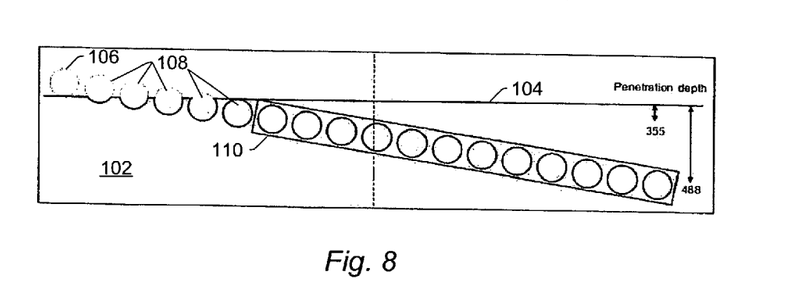
FIG. 8 is a schematic diagram illustrating a cross-sectional view of one example of different types of defects on a wafer and the positions of the different types of defects with respect to the penetration depths of different wavelengths of light.

FIG. 8 illustrates one example of different types of defects on a wafer and the positions of the different types of defects with respect to the penetration depths of different wavelengths of light. As shown in FIG. 8, different wavelengths of light penetrate to different depths within wafer 102. In particular, as shown in FIG. 8, the penetration depth (e.g., about 10 nm) of ultraviolet light at 355 nm below upper surface 104 of wafer 102 is much less than the penetration depth (e.g., about 500 nm) of visible light at 488 nm below upper surface 104 of wafer 102.

As shown in FIG. 8, different types of defects have different spatial relationships with respect to upper surface 104 of the wafer. In particular, defect 106 is not located below upper surface 104. Therefore, defect 106 is a surface defect. Defects 108 are located partially below the upper surface 104 of the wafer. In this manner, defects 108 are also surface defects. In addition, defects 110 are entirely located below the upper surface of the wafer. As such, defects 110 are subsurface defects (e.g., subsurface COPs). It is noted that the positions of the defects with respect to each other and with respect to the upper surface of the wafer as shown in FIG. 8 merely to illustrate the different interactions of different types of defects with light at different wavelengths. Wafers being inspected will have defects at various positions with respect to the upper surface of the wafer and various positions with respect to one another.

As can be seen from FIG. 8, light at ultraviolet wavelengths will not be scattered (or will not be substantially scattered) from defects 110 since the depth to which the ultraviolet light penetrates into wafer 102 is shallower than the positions of these defects within the wafer thereby substantially preventing the ultraviolet light from impinging on defects 110. However, light at visible wavelengths will be scattered from defects 110 since the depth to which the visible light penetrates into wafer 102 is below the upper surface of these defects thereby allowing the visible light to impinge upon and be scattered from defects 110.

The following example is not to be construed in any way as a limiting embodiment of the invention and is included herein for example purposes only to generally illustrate the capability of the system and method embodiments described herein.

EXAMPLE

Discrimination Between Surface and Subsurface Defects

Wafers that contained both surface defects and subsurface defects (wafers that were known to be COP-rich) were inspected with different wavelengths of light by inspection tools that otherwise had relatively similar optical configurations. For instance, the wafers were inspected at a wavelength of 488 nm by a first tool. The wafers were also inspected at a wavelength of 355 nm by a second tool. The inspections at both wavelengths were performed at an oblique angle of incidence.

After inspection, some of the detected defects were reviewed by a SEM. The SEM used in these experiments was an ev300 system that is commercially available from KLA-Tencor. As is known in the art, a SEM cannot re-detect defects that have been detected by optical inspection and that are located below the upper surface of the wafer. Therefore, the SEM was used to verify if the defects were surface or subsurface defects. In other words, defects re-detected by the SEM can be classified as surface defects, and defects not re-detected by the SEM can be classified as subsurface defects.

The results of the inspections and defect review are illustrated in Table 1.

TABLE 1

|  | Found in SEM | Cannot Be Found in SEM | Total Reviewed |
|---|---|---|---|
| Common for first and second tools | 50 | 2 | 52 |
| Unique to second tool | 61 | 5 | 66 |
| Unique to first tool | 1 | 99 | 100 |

As shown in Table 1, COP defects that are common for the first and second tools (i.e., COP defects that were detected by both the first and second tools) included 50 that were re-detected or "found" by defect review performed by the SEM and 2 that could not be found by defect review performed by the SEM. The two defects that could not be found by defect review are likely relatively shallow subsurface ("embedded") COPs (i.e., COPs located entirely below the surface of the wafer but also relatively close to the surface of the wafer). Therefore, of the defects that were found by inspection using a visible wavelength that penetrates into the wafer and by inspection using an ultraviolet wavelength that does not penetrate into the wafer, almost all were verified by defect review as being surface defects.

As further shown in Table 1, 66 defects that were only detected by the second tool (Unique to second tool) were reviewed by the SEM, and only 5 could not be re-detected by the SEM. These unique defects may not have been re-detected because they were too small or were relatively shallow embedded COP defects. The defect review results, therefore, indicate that most of the defects detected only at the ultraviolet wavelength that does not substantially penetrate into the wafer were surface defects. As further shown in Table 1, 100 defects that were only detected by the first tool (Unique to first tool) were reviewed by the SEM, and only 1 could be re-detected by the SEM, which indicates that 99 of the 100 defects that were reviewed are completely subsurface COP defects. The defect review results, therefore, indicate that most of the defects detected only at the visible wavelength that penetrates into the wafer were subsurface defects.

The results described above, therefore, verify that ultraviolet and visible light may be used to discriminate between surface and subsurface defects. In particular, 99% of the COP defects seen only in the inspection performed by the first tool at a wavelength of 488 nm were not found by SEM defect review thereby indicating that these defects are subsurface defects. Therefore, defects that are detected at the penetrating wavelength and not at the substantially non-penetrating wavelength may be identified as subsurface defects by the system and method embodiments described herein. In contrast, COP defects that are common to the inspections performed by the first and second tools, or found only by inspection performed by the second tool at a wavelength of 355 nm, were easily found during the SEM defect review thereby confirming that these defects are surface defects or "surface-breaking" defects.

Another embodiment relates to a method for inspection of a wafer. The method includes illuminating the wafer with light at a first wavelength that penetrates into the wafer and light at a second wavelength that does not substantially penetrate into the wafer. The method also includes generating output signals responsive to light from the wafer resulting from the illuminating step. In addition, the method includes detecting defects on the wafer using the output signals. The method further includes determining if the defects are subsurface defects or surface defects using the output signals. These steps may be performed using any of the system embodiments described herein.

In one embodiment, the first wavelength is a visible wavelength, and the second wavelength is an ultraviolet wavelength. As described further herein, the first and second wavelengths may be selected based on one or more characteristics of the materials that are being inspected. In some embodiments, illuminating the wafer with the light at the first and second wavelengths is performed sequentially. In other embodiments, illuminating the wafer with the light at the first and second wavelengths is performed simultaneously. Illuminating the wafer with multiple wavelengths sequentially or simultaneously may be performed by any of the system embodiments described herein. In another embodiment, the illuminating step includes directing the light at the first and second wavelengths to the wafer at substantially the same angle of incidence. Such illumination may be provided by the systems shown in FIGS. 1 and 4. In a different embodiment, the illuminating step includes directing the light at the first and second wavelengths to the wafer at different angles of incidence. Such illumination may be provided by the systems shown in FIGS. 2-3 and 5-7.

In an embodiment, the light from the wafer includes scattered light. In another embodiment, the generating step includes collecting the light from the wafer at multiple sets of solid angles. Collecting the light from the wafer at multiple sets of solid angles may be performed using the systems shown in FIGS. 6 and 7.

In some embodiments, the method includes determining a lateral dimension of the defects using the output signals. Determining the lateral dimension of the defects may be performed as described herein. In another embodiment, the method includes determining a depth of the subsurface defects within the wafer using the output signals. Determining the depth of the subsurface defects within the wafer may be performed as described further herein. In a further embodiment, the determining step includes comparing the output signals responsive to the light returned from the wafer resulting from illuminating the wafer with the light at the first wavelength and the output signals responsive to the light returned from the wafer resulting from illuminating the wafer with the light at the second wavelength as a function of location on the wafer. Comparing the output signals may be performed as described further herein. Each of the embodiments of the method described above may include any other step(s) described herein. In addition, each of the embodiments of the method described above has all of the advantages of the systems described above.

The results of the inspection performed by the methods and systems described herein may be used to alter a parameter of a process or a process tool using a feedback control technique, a feedforward control technique, and/or an in situ control technique. The parameter of the process or the process tool may be altered manually or automatically.

Further modifications and alternative embodiments of various aspects of the invention may be apparent to those skilled in the art in view of this description. For example, methods and systems for inspection of a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method for inspection of a wafer, comprising:
    illuminating the wafer with light at a first wavelength that penetrates into the wafer and light at a second wavelength that does not substantially penetrate into the wafer, wherein said illuminating comprises directing the light at the first and second wavelengths to the wafer at substantially the same angle of incidence;
    generating output signals responsive to light from the wafer resulting from said illuminating, wherein said generating comprises collecting and detecting the light from the wafer at multiple sets of solid angles;
    detecting defects on the wafer using the output signals;
    determining if the defects are subsurface defects or surface defects using the output signals;
    determining a lateral dimension of the subsurface defects using only the output signals corresponding to the light from the wafer at the first wavelength; and
    determining a lateral dimension of the surface defects using only the output signals corresponding to the light from the wafer at the second wavelength.

2. The method of claim 1, wherein the first wavelength is a visible wavelength, and wherein the second wavelength is an ultraviolet wavelength.

3. The method of claim 1, wherein said illuminating the wafer with the light at the first and second wavelengths is performed sequentially.

4. The method of claim 1, wherein said illuminating the wafer with the light at the first and second wavelengths is performed simultaneously.

5. The method of claim 1, wherein the light from the wafer comprises scattered light.

6. The method of claim 1, further comprising determining a depth of the subsurface defects within the wafer using the output signals.

7. The method of claim 1, wherein said determining if the defects are subsurface defects or surface defects comprises comparing the output signals responsive to the light returned from the wafer resulting from said illuminating the wafer with the light at the first wavelength and the output signals responsive to the light returned from the wafer resulting from said illuminating the wafer with the light at the second wavelength as a function of location on the wafer.

8. A system configured to inspect a wafer, comprising:
    an illumination subsystem configured to illuminate the wafer with light at a first wavelength that penetrates into the wafer and light at a second wavelength that does not substantially penetrate into the wafer, wherein the illumination subsystem is further configured to illuminate the wafer by directing the light at the first and second wavelengths to the wafer at substantially the same angle of incidence;
    a detection subsystem configured to generate output signals responsive to light from the wafer resulting from illumination of the wafer, wherein the detection subsystem is further configured to collect and detect the light from the wafer at multiple sets of solid angles; and
    a processing subsystem configured to detect defects on the wafer using the output signals to determine if the defects are subsurface defects or surface defects using the output signals, to determine a lateral dimension of the subsurface defects using only the output signals corresponding to the light from the wafer at the first wavelength, and to determine a lateral dimension of the surface defects using only the output signals corresponding to the light from the wafer at the second wavelength.

9. The system of claim 8, wherein the illumination subsystem comprises a single light source.

10. The system of claim 8, wherein the illumination subsystem comprises more than one light source, wherein one of the more than one light source is configured to generate the light at the first wavelength, and wherein another of the more than one light source is configured to generate the light at the second wavelength.

11. The system of claim 8, wherein the first wavelength is a visible wavelength, and wherein the second wavelength is an ultraviolet wavelength.

12. The system of claim 8, wherein the illumination subsystem is further configured to illuminate the wafer with the light at the first and second wavelengths sequentially.

13. The system of claim 8, wherein the illumination subsystem is further configured to illuminate the wafer with the light at the first and second wavelengths simultaneously.

14. The system of claim 8, wherein the light from the wafer comprises scattered light.

15. The system of claim 8, wherein the processing subsystem is further configured to determine a depth of the subsurface defects within the wafer using the output signals.

16. The system of claim 8, wherein the processing subsystem is further configured to compare the output signals responsive to the light returned from the wafer resulting from the illumination of the wafer with the light at the first wavelength and the output signals responsive to the light returned from the wafer resulting from the illumination of the wafer with the light at the second wavelength as a function of location on the wafer.

17. A carrier medium, comprising program instructions executable on a computer system for performing a method for detecting defects on a wafer, wherein the method comprises:
    detecting first defects on the wafer using first output signals responsive to light from the wafer resulting from illumination of the wafer with light at a first wavelength that penetrates into the wafer;
    detecting second defects on the wafer using second output signals responsive to light from the wafer resulting from illumination of the wafer with light at a second wavelength that does not substantially penetrate into the wafer, wherein the illumination at the first and second wavelengths is directed to the wafer at substantially the same angle of incidence, and wherein the first and second output signals are generated by collecting and detecting the light from the wafer at multiple sets of solid angles;
    determining if the first and second defects are subsurface defects or surface defects using the first and second output signals generated at approximately the same location on the wafer in combination;
    determining a lateral dimension of the subsurface defects using only the first output signals; and
    determining a lateral dimension of the surface defects using only the second output signals.

18. The carrier medium of claim 17, wherein the first wavelength is a visible wavelength, and wherein the second wavelength is an ultraviolet wavelength.

19. The carrier medium of claim 17, wherein the light from the wafer resulting from the illumination of the wafer with the light at the first and second wavelengths comprises scattered light.

20. The carrier medium of claim 17, wherein the method further comprises determining a depth of the subsurface defects within the wafer using the first output signals.

21. The carrier medium of claim 17, wherein said determining if the first and second defects are subsurface defects or surface defects comprises comparing the first and second output signals as a function of location on the wafer.

* * * * *